United States Patent [19]

Barzaghi et al.

[11] 4,195,088
[45] Mar. 25, 1980

[54] 1,3-DIHYDRO-IMIDAZO-(4,5-B)-PYRIDIN-2-ONES

[75] Inventors: Fernando Barzaghi, Monza; Mario Bianchi, Carate Brianza, both of Italy

[73] Assignee: Roussel Uclaf, Paris, France

[21] Appl. No.: 972,942

[22] Filed: Dec. 26, 1978

[30] Foreign Application Priority Data

May 10, 1978 [IT] Italy .................. 49289 A/78

[51] Int. Cl.² .................. A61K 31/435; C07D 235/00
[52] U.S. Cl. ...................... 424/256; 546/118
[58] Field of Search .................. 546/118; 424/256

[56] References Cited

U.S. PATENT DOCUMENTS 3,401,030  9/1968  Berthold et al. .................. 546/118

Primary Examiner—Alan L. Rotman
Assistant Examiner—Robert C. Whittenbaugh
Attorney, Agent, or Firm—Hammond & Littell, Weissenberger and Muserlian

[57] ABSTRACT

Novel 1,3-dihydro-imidazo-(4,5-b)-pyridin-2-ones of the formula

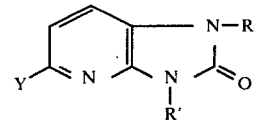

wherein R is alkyl of 1 to 3 carbon atoms and R' is pyridyl and Y is selected from the group consisting of hydrogen and chlorine and their non-toxic, pharmaceutically acceptable acid addition salts having gastric antisecretic and anti-ulcerogenic and anorexigenic activity and a novel process and novel intermediates for their preparation.

26 Claims, No Drawings

1,3-DIHYDRO-IMIDAZO-(4,5-B)-PYRIDIN-2-ONES

STATE OF THE ART

Various 1,3-dihydro-imidazo-(4,5-b)-pyridin-2-ones are known. U.S. Pat. No. 3,719,683 describes such products as antidepressants and French Pat. No. 2,312,248 also describes compounds of this type as being analgesics, anti-pyretics and anti-inflammatory agents.

OBJECTS OF THE INVENTION

It is an object of the invention to provide the novel compounds of formula I and their non-toxic, pharmaceutically acceptable acid addition salts.

It is another object of the invention to provide a novel process for the preparation of the compounds of formula I and novel intermediates therefor.

It is an additional object of the invention to provide novel gastric anti-secretric and anti-ulcerogenic compositions and a method of reducing gastric secretion and ulcers in warm-blooded animals.

It is a further object of the invention to provide novel anorexigenic compositions and to provide a novel method of curbing the appetites of warm-blooded animals.

These and other objects and advantages of the invention will become obvious from the following detailed description.

THE INVENTION

The novel 1,3-dihydro-imidazo-(4,5-b)-pyridin-2-ones of the invention are selected from the group consisting of compounds of the formula

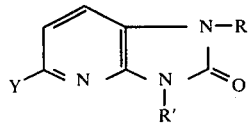

wherein R is alkyl of 1 to 3 carbon atoms and R' is pyridyl and Y is selected from the group consisting of hydrogen and chlorine and their non-toxic, pharmaceutically acceptable acid addition salts.

Examples of alkyl in the compounds of formula I are methyl, ethyl, propyl and isopropyl. The pyridyl group may be attached to the nitrogen atom of the 1,3-dihydro-imidazo-(4,5-b)-pyridine ring through any one of the carbon atoms in the pyridyl ring.

Examples of suitable acids for the preparation of the non-toxic, pharmaceutically acceptable acid addition salts are mineral acids such as hydrochloric acid, hydrobromic acid, hydroiodic acid, nitric acid, sulfuric acid and phosphoric acid and organic acids such as acetic acid, formic acid, benzoic acid, citric acid, maleic acid, fumaric acid, succinic acid, tartaric acid, oxalic acid, glyoxylic acid, aspartic acid, alkylmonosulfonic acids such as methane sulfonic acid, ethane sulfonic acid and propane sulfonic acid and alkyldisulfonic acids such as methanedisulfonic acid and $\alpha,\beta$-ethanedisulfonic acid, arylmonosulfonic acids such as benzenesulfonic acid and aryldisulfonic acids.

Among the preferred compounds of formula I are 1-methyl-3-(4-pyridyl)-1,3-dihydro-imidazo-(4,5-b)-pyridin-2-one, 1-methyl-3-(3-pyridyl)-5-chloro-1,3-dihydro-imidazo-(4,5-b)-pyridin-2-one and 1-methyl-3-(2-pyridyl)-5-chloro-1,3-dihydro-imidazo-(4,5-b)-pyridin-2-one and their non-toxic, pharmaceutically acceptable acid addition salts.

The novel process of the invention for the preparation of compounds of formula I comprises subjecting a compound of the formula

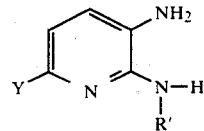

wherein Y and R' have the above definition to cyclization conditions to obtain a compound of the formula

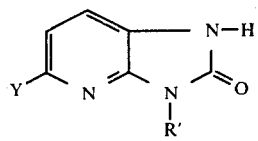

and reacting the latter with a compound of the formula

R-X      IV where R has the above definition and X is selected from the group consisting of chlorine, bromine, iodine, methylsulfate and ethylsulfate to obtain the corresponding compound of formula I, which may then be reacted, if desired, with a non-toxic, pharmaceutically acceptable acid to form the corresponding acid addition salt.

One means of effecting the cyclization is to react a compound of formula II with an alkyl chloroformate of the formula Cl—COOAlK wherein AlK is alkyl of 1 to 3 carbon atoms to form a compound of the formula

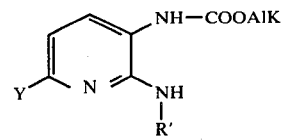

wherein R' and Y have the above definition which is then reacted with a basic agent. Another means of effecting the cyclization is to react a compound of formula II with an alkyl iminocarboxylate of the formula

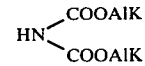

wherein AlK is alkyl of 1 to 3 carbon atoms to obtain a compound of the formula

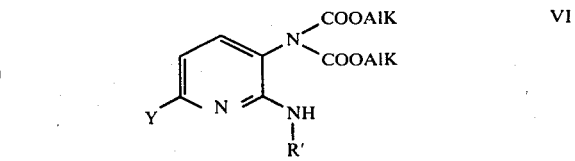

wherein R' and Y have the above definitions and reacting the latter with a basic agent.

Other means of effecting the cyclization comprise reacting the compound of formula II with phosgene under reaction conditions analogous to those of J.A.C.S., Vol. 80 (1958), p. 1659 or reacting at high temperature the compound of formula II with urea under the conditions of the above J.A.C.S. article or French Pat. No. 2,113,192 or by reacting the compound of formula II with carbonyldiimidazole, preferably with heating.

Among the preferred reaction conditions, the product of formula III is reacted with a basic agent and then with the product of formula IV in an organic solvent at temperatures from room temperature to reflux. Examples of suitable organic solvents are methanol, ethanol, propanol, ether, benzene, xylene, toluene, dimethylacetamide, dimethylformamide, dioxane, tetrahydrofuran, acetone and chloroform.

Examples of suitable bases are alkali metal hydroxides such as sodium hydroxide, lithium hydroxide or potassium hydroxide; alkali metal carbonates such as sodium carbonate or potassium carbonate; alkali metal akylates such as sodium methylate, sodium ethylate or potassium ethylate; alkali metal hydrides such as sodium hydride or potassium hydride; alkali metal amides such as sodium amide, potassium amide or lithium amide; sodium and alkali metal acetates such as sodium acetate or potassium acetate.

The salification of the compounds of formula I may be effected by known methods in one or more solvents such as ether, ethanol or methanol.

When the cyclization is effected with an alkyl chloroformate, the reaction is preferably effected in an organic solvent in the presence of a basic agent at temperatures from room temperature to reflux. Examples of suitable solvents are chloroform, benzene, toluene, cyclohexane, tetrahydrofuran and ether and examples of the basic agent are alkali metal alkylates such as sodium methylate, sodium ethylate, potassium ethylate and potassium tert.-butylate.

The compounds of formula I may also be prepared by reacting at room temperature to reflux a compound of the formula

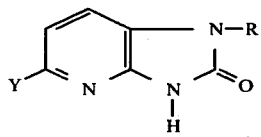

VII wherein R and Y have the above definitions with a compound of the formula

R'—X    VIII wherein R' is pyridyl and X is selected from the group consisting of chlorine, bromine and iodine to obtain the corresponding compound of formula I which may, if desired, be salified with an acid to form the acid addition salt.

The compound of formula VII is preferably reacted firstly with a basic agent and then with an excess of the compound of formula VIII in an organic solvent.

Examples of suitable organic solvents are methanol, ethanol, propanol, ether, benzene, xylene, toluene, dimethylformamide, dioxane, tetrahydrofuran, dimethylsulfoxide, hexamethylphosphortriamide, acetone, chloroform, pyridine, dimethylacetamide, diethyleneglycol dimethylether.

Examples of suitable bases are alkali metal hydroxides such as sodium hydroxide, lithium hydroxide or potassium hydroxide, alkali metal carbonates such as sodium carbonate or potassium carbonate; alkali metal alkylates such as sodium methylate, sodium ethylate or potassium ethylate, alkali metal hydrides such as sodium hydride or potassium hydride, alkali metal amides such as sodium amide, potassium amide or lithium amide, sodium and alkali metal acetates such as sodium acetate or potassium acetate.

The reaction of compounds of formulae VII and VIII may also be effected in an organic solvent in the presence of a catalyst such as copper or a cuprous salt like cuprous chloride or mixtures thereof at temperatures from room temperature to reflux. Examples of suitable organic solvents are pyridine, dimethylformamide, dimethylacetamide, diethyleneglycoldimethyl ether, dimethylsulfoxide, and hexamethylphosphortriamide. The reaction is preferably effected in the presence of a base such as potassium acetate or sodium hydride.

The novel therapeutic compositions of the invention are comprised of an anti-ulcerously and gastric anti-secretically effective amount or an anorexigenically effective amount of at least one compound of formula I and its non-toxic, pharmaceutically acceptable acid addition salts and an inert pharmaceutical carrier or excipient. The composition may be in the form of tablets, dragees, gelules, granules, suppositories and injectable solutions or suspensions.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

The compositions of the invention have the ability to reduce the volume of gastric secretions and their acidity and are useful for the treatment of hyperchlorohydrity, gastritis, gastric ulcers, hiatales hernias and gastroduodenal affections accompanied by gastric hyperacidity.

The compositions also have anorexigenic activity and are useful for the treatment of simple obesity in adults, plethoric states, obesity complicated by diabetic and hypertension, post-gravidic obesity and obesity in infants.

Among the preferred compositions of the invention are those containing as the active compounds of formula I compounds wherein R is methyl and especially 1-methyl-3-(4-pyridyl)-1,3-dihydro-imidazo-(4,5-b)-pyridin-2-one, 1-methyl-3-(3-pyridyl)-5-chloro-1,3-dihydro-imidazo-(4,5-b)-pyridin-2-one and 1-methyl-3-(2-pyridyl)-5-chloro-1,3-dihydro-imidazo-(4,5-b)-pyridin-2-one and their non-toxic, pharmaceutically acceptable acid addition salts.

The novel method of inducing gastric anti-secretion and anti-ulcerogenic activity in warm-blooded animals, including humans, comprises administering to warm-blooded animals a gastric anti-secretically and anti-ulcerogenically effective amount of at least one compound of formula I and its non-toxic, pharmaceutically acceptable acid addition salts. The novel method of inducing anorexigenic activity in warm-blooded animals, including humans, comprises administering to warm-blooded animals an anorexigenically effective amount of at least one compound of formula I and its non-toxic, pharmaceutically acceptable acid addition salts. The compounds may be administered orally, rectally or parenterally. The usual daily dose is 1 to 40 mg/kg depending on the compound and the method of administration.

The novel intermediate compounds of the invention have the formula

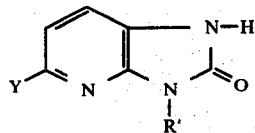

wherein R' is pyridyl and Y is hydrogen or chlorine and their acid addition salts as well as 2-(4-pyridylamino)-3-amino-pyridine, 2-(2-pyridylamino)-3-amino-pyridine and 2-(2-pyridylamino)-3-nitro-pyridine.

The compounds of formula II may be prepared by a process analogous to that of French Pat. No. 1,447,539 or by reacting a compound of the formula

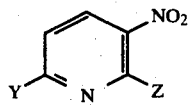

wherein Y is hydrogen or chlorine and Z is nitro or chlorine with a compound of the formula $NH_2-R''$ wherein R'' is pyridyl, preferably in an organic solvent such as ethanol or cyclohexane to obtain a compound of the formula

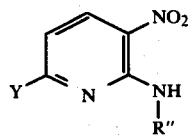

which is then reacted with a reducing agent such as hydrogen in the presence of Raney nickel or platinum oxide to obtain the corresponding compound of formula II.

The compounds of formula VII are generally known and may be prepared by a process analogous to that of French Pat. No. 2,150,820.

In the following examples there are described several preferred embodiments to illustrate the invention. However, it is to be understood that the invention is not intended to be limited to the specific embodiments.

EXAMPLE 1

1-methyl-3-(4-pyridyl)-1,3-dihydro-imidazo-(4,5-b)-pyridin-2-one

STEP A: 2-(4-pyridylamino)-3-amino-pyridine

A solution of 16.5 g of 2-(4-pyridylamino)-3-nitro-pyridine in 400 ml of 95% ethanol containing 1.6 g of 10% palladized carbon was hydrogenated at 30°–40° C. at atmospheric pressure until 5.8 liters of hydrogen were absorbed and the mixture was filtered to remove the catalyst. The filtrate was evaporated to dryness and the residue was taken up in petroleum ether. The mixture was filtered to obtain 13.5 g (95% yield) of raw product melting at 202°–204° C. which was crystallized from 95% ethanol to obtain 2-(4-pyridylamino)-3-amino-pyridine in the form of a pale yellow, crystalline powder melting at 203°–205° C.

Analysis: $C_{10}H_{10}N_4$:
Calculated: %C 64.50; %H 5.41; %N 30.09; Found: %C 64.46; %H 5.20; %N 29.80.

STEP B:
3-(4-pyridyl)-1,3-dihydro-imidazo-(4,5-b)-pyridin-2-one 18 g of N,N'-carbonyldiimidazole were added to a solution of 13.5 g of the product of Step A in 350 ml of chloroform and the mixture was refluxed for 8 hours and was then cooled. The mixture was evaporated to dryness and the residue was taken up in 400 ml of water. The resulting solution was neutralized with 2 N hydrochloric acid and was then filtered. The recovered product was rinsed with water to obtain 14 g (91.6% yield) of raw product melting at 265°–267° C. The product was crystallized from 95% ethanol and dried under reduced pressure at 110° C. for 6 hours to obtain white supple needles of 3-(4-pyridyl)-1,3-dihydro-imidazo-(4,5-b)-pyridin-2-one melting at 265°–267° C.

Analysis: $C_{11}H_8N_4O$:
Calculated: %C 62.26; %H 3.80; %N 26.40; Found: %C 61.98; %H 3.66; %N 26.22.

STEP C:
1-methyl-3-(4-pyridyl)-1,3-dihydro-imidazo-(4,5-b)-pyridin-2-one 5.7 g of sodium hydroxide pastilles were added to a suspension of 15 g of the product of Step B in 700 ml of methanol and complete dissolution occured after a few minutes. The mixture was stirred at room temperature for an hour and after the addition of 45.6 g of methyl iodide thereto, the mixture was stirred at room temperature for another 6 hours. The mixture stood overnight and was then filtered to remove hydroiodide of product melting at 275°–285° C. The filtrate was evaporated to dryness and the combined residue and hydroiodide were dissolved in water. The solution was made alkaline by addition of 30% sodium hydroxide solution and was then extracted with chloroform. The organic phase was dried over anhydrous sodium sulfate and was filtered. The filtrate was evaporated to dryness and the residue was crystallized from 95% ethanol to obtain 4 g (25% yield) of 1-methyl-3-(4-pyridyl)-1,3-dihydro-imidazo-(4,5-b)-pyridin-2-one in the form of a pale crystalline powder melting at 211°–213° C.

Analysis: $C_{12}H_{10}N_4O$: Calculated: %C 63.71 %H 4.46; %N 24.77; Found: %C 64.02; %H 4.54; %N 25.03.

EXAMPLE 2

1-methyl-3-(2-pyridyl)-1,3-dihydro-imidazo-(4,5-b)-pyridin-2-one

STEP A: 2-(2-pyridylamino)-3-nitro-pyridine 31.6 g of 2-chloro-3-nitro-pyridine and 56.5 g of 2-amino-pyridine were well mixed in a mortar and the mixture was slowly heated on an oil bath to the melting point. At 150° C. a lively reaction started and the temperature spontaneously rose to 160° C. The heating was suspended until the isothermic reaction ceased and heating at 150° C. was continued for 2 hours. The mixture was cooled and the fused mass was taken up in 500 ml of chloroform. The mixture was concentrated and was chromatographed over silica gel. Elution with about 3 liters of a 1–0.75–1.2 chloroform-benzene-ether mixture yielded unreacted 2-chloro-3-nitro-pyridine and evaporation of the eluent yielded 20 g of raw product which was crystallized from 95% ethanol to obtain 15.5 g (36% yield) of 2-(2-pyridylamino)-3-nitro-pyridine in the form of orange-yellow needles melting at 121°–123° C. The product was soluble in 2 N hydrochloric acid.

Analysis: $C_{10}H_8N_4O_2$: Calculated: %C 55.55; %H 3.73; %N 25.92; Found: %C 55.85; %H 3.33; %N 25.72.

STEP B: 2-(2-pyridylamino)-3-amino-pyridine

A solution of 18.3 g of the product of Step A in 550 ml of 95% ethanol containing 1.6 g of 10% palladized carbon was hydrogenated at atmosphere pressure at room temperature until 6.3 liters of hydrogen were absorbed (about one hour) and the mixture was filtered to remove the catalyst. The filtrate was evaporated to dryness under reduced pressure and the 15.8 g of residue (98.6% yield) which was easily changed in air was used for the next step immediately.

STEP C:
3-(2-pyridyl)-1,3-dihydro-imidazo-(4,5-b)-pyridin-2-one

A mixture of 15.8 g of the product of Step B, 20.8 g of N,N'-carbonyldiimidazole in 175 ml of anhydrous chloroform was refluxed for 8 hours and was then cooled and evaporated to dryness. The residue was taken up in 300 ml of water and the solution was neutralized with 2 N hydrochloric acid. The mixture was filtered and the recovered product was washed with ice water to obtain 16 g (89% yield) of 3-(2-pyridyl)-1,3-dihydro-imidazo-(4,5-b)-pyridin-2-one in the form of colorless chips melting at 235°–238° C. Two crystallizations from xylene did not change the melting point.

Analysis: $C_{11}H_8N_4O$: Calculated: %C 62.26; %H 3.80; %N 26.40; Found: %C 62.35; %H 3.87; %N 26.03.

STEP D:
1-methyl-3-(2-pyridyl)-1,3-dihydro-imidazo-(4,5-b)-pyridin-2-one

A suspension of 10.6 g of the product of Step C and 5 g of sodium hydroxide pastilles in 800 ml of methanol was refluxed for 30 minutes and the mixture was then stirred at room temperature until complete dissolution occured (about 2 hours). 45.6 g of methyl iodide were then added dropwise and the mixture was stirred for another 4 hours at room temperature and then allowed to stand overnight. The mixture was evaporated to dryness and the residue was dissolved in 700 ml of water. The aqueous phase was made alkaline with 30% sodium hydroxide solution and was extracted with chloroform. The organic phase was dried over anhydrous sodium sulfate and was filtered and the filtrate was evaporated to dryness. The residue was taken up in petroleum ether and the mixture was filtered. The product was crystallized from an xylene-petroleum ether mixture to obtain 7 g (62% yield) of 1-methyl-3-(2-pyridyl)-1,3-dihydro-imidazo-(4,5-b)-pyridin-2-one in the form of lightly colored pale yellow crystals melting at 128°–130° C.

Analysis: $C_{12}H_{10}N_4O$: Calculated %C 63.71; %H 4.45; %N 24.77; Found: %C 64.00; %H 4.46; %N 24.49.

EXAMPLE 3

1-methyl-3-(2-pyridyl)-5-chloro-1,3-dihydro-imidazo-(4,5-b)-pyridin-2-one 7.36 g of 1-methyl-5-chloro-1,3-dihydro-imidazo-(4,5-b)-pyridin-2-one were dissolved in 160 ml of hot dimethylformamide and after cooling the solution to 30° C., 4.64 g of a 50% sodium hydride-oil suspension were slowly added thereto. The mixture was stirred at 30° C. for 2 hours and then 80 ml or 129.6 g of 2-bromo-pyridin and 1.2 g of cuprous chloride were added thereto. The mixture was refluxed for 4 hours and was then cooled and evaporated to dryness. The residue was taken up in ammonium hydroxide solution and the mixture was extracted with chloroform. The organic phase was dried and evaporated to dryness and the residue was taken up in petroleum ether. The mixture was filtered and the product was crystallized from 95% ethanol to obtain 6.5 g of 1-methyl-3-(2-pyridyl)-5-chloro-1,3-dihydroimidazo-(4,5-b)-pyridin-2-one in the form of white crystals melting at 192°–194° C.

Analysis: $C_{12}H_9ClN_4O$: Calculated: %C 55.29; %H 3.48; %N 21.49; Found: %C 55.50; %H 3.60; %N 21.42.

EXAMPLE 4

1-methyl-3-(3pyridyl)-5-chloro-1,3-dihydroimidazo-(4,5-b)-pyridin-2-one 7.36 g of 1-methyl-5-chloro-1,3-dihydro-imidazo-(4,5-b)-pyridin-2-one were dissolved in 160 ml of hot dimethylformamide and after cooling the solution to 30° C., 4.64 g of a 50% sodium hydride-oil suspension were slowly added thereto. The mixture was stirred at 40°–50° C. for 2 hours and then 80 ml or 128.8 g of 3-bromo-pyridine and 1.5 g of cuprous chloride were added thereto. The mixture was refluxed for 9 hours and was then cooled and evaporated to dryness. The residue was taken up in ammonium hydroxide solution and was filtered. The product was washed with water to obtain 8 g of raw product which was dissolved in acetone. The solution was chromatographed over silica gel and was eluted with acetone. The product was crystallized from 95% ethanol to obtain 5 g of 1-methyl-3-(3-pyridyl)-5-chloro-1,3-dihydro-imidazo-(4,5-b)-pyridin-2-one in the form of white needles melting at 206°–208° C.

Analysis: $C_{12}H_9ClN_4O$: Calculated: %C 55.29; %H 3.48; %N 21.49; Found: %C 55.18; %H 3.69; %N 21.69.

EXAMPLE 5

Tablets were prepared containing 300 mg of 1-methyl-3-(3-pyridyl)-5-chloro-1,3-dihydro-imidazo-(4,5-b)-pyridin-2-one and sufficient excipient of lactose, starch, talc and magnesium stearate for a final tablet weight of 500 mg.

Gelules were prepared containing 200 mg of 1-methyl-3-(2-pyridyl)-5-chloro-1,3-dihydro-imidazo-(4,5-b)-pyridin-2-one and sufficient excipient of talc, magnesium stearate and aerosil for a final weight of 500 mg.

PHARMACOLOGICAL DATA

A. Gastric anti-secretic activity

The test procedure of Shay et al [Gastroenterology, Vol. 5 (1945), p. 43] was used with male rats weighing about 200 g of having been deprived of food for 48 hours, but having at their disposal drinking water containing 8% glucose. The pylore was ligated in the rats lightly anesthesized with ether and after the operation, the test products were administered in varying doses in a 0.5% carboxymethyl cellulose solution intraduodenally and then the abdominal incission was sutured. The control animals received only the 0.5% carboxymethyl cellulose solution. After 3 hours, the animals were killed and their stomachs were removed beyond the esophagus ligature and the gastric juice was removed and was centrifuged. The volume of the juice was returned to its original volume and 100 $\mu$l of gastric juice was analyzed for its total acidity by titration to a pH of 7 with N/10 sodium hydroxide solution. The percent variation in the volume and total acidity of the gastric secretions was determined with respect to the control animals. The total acidity was expressed in concentration and acid output with the latter calculated in multiplying acid concentration by secretion volume. The results are reported in Table I.

TABLE I

| Product of Example | Doses in mg/Kg | % Variation | | |
|---|---|---|---|---|
| | | Volume | Total Acidity | |
| | | | Concentration | Acid output |
| 3 | 100 | −88 | −28 | −93 |
| | 12.5 | −61 | −17 | −61 |
| | 6.2 | −50 | −23 | −61 |
| 4 | 100 | −85 | −26 | −88 |
| | 12.5 | −56 | −46 | −72 |
| | 6.2 | −70 | −13 | −75 |

B. Antiulcerous Activity

The test of Senay et al [Proc. Soc. Exp. Biol., Vo. 124 (1967), p. 1221] was effected on groups of 5 female rats weighing 150 g by inducing stomach ulcers under stress (cold and constrained). The animals were held without food but with water for 48 hours and were then given water containing glucose for 8 hours and the animals received with an esophagus probe the test products in an 0.5% carboxymethyl cellulose solution. The controls received only the 0.5% carboxymethyl cellulose solution and after 2 hours, the animals were placed in a grilled corset and their paws were tied and placed in a refrigerator for 2 hours at 8° C. The rats were freed and killed and their stomachs were removed, opened at the great bend. The stomach was examined with binocular magnifying glass and the gravity of the lesions was noted on a scale 0 to 3 for each stomach. The average intensity of the ulcerations was determined for each group of rats and the degree of ulceration for each group as compared to the controls and the number of animals presenting a gastric hemorrhage as compared to the controls was determined. The results are reported in Table II.

TABLE II

| Product of Example | Doses in mg/Kg | Degree of ulceration (controls = 1) | No. of rats presenting a gastric hemorrhage /treated rats |
|---|---|---|---|
| 1 | 25 | 0.05 | 0/5 |
| 2 | 25 | 0.10 | 1/5 |
| 3 | 25 | 0.36 | 0/5 |
| 4 | 12.5 | 0.23 | 0/5 |
| | 25 | 0 | 0/5 |

Anorexigenic Activity

Groups of 5 rats for 7 days consumed their daily meal in 4 hours and received voluntary drinking water. The test product was orally administered at a dose of 25 mg/kg in 0.5% carboxymethyl cellulose. The controls received only the 0.5% carboxymethyl cellulose solution and one hour after the administration, the animals were given their meal. The percentage of food consumed one hour and 4 hours after presentation of the meals was compared with the controls and the results are reported in Table III.

TABLE III

| Product of Example | % Consumption of food after | |
|---|---|---|
| | 1 Hour | 4 Hours |
| 2 | 54 | 79 |
| 3 | 35 | 84 |
| 4 | 52 | 81 |

D. Acute Toxicity

The acute toxicity was determined on groups of 5 and 10 male mice weighing between 20 to 22 g fasting from the day before the test. The products were orally administered in a 0.5% methyl cellulose solution with an esophagus probe and the number of dead was determined daily for one week. The $DL_{50}$ dose was determined to be ≃500 mg/kg for the product of Example 1 and > 1000 mg/kg for the products of Examples 2,3 and 4.

Various modifications of the products and methods of the invention may be made without departing from the spirit or scope thereof and it is to be understood that the invention is to be limited only as defined in the appended claims. We claim:

1. A compound selected from the group consisting of the formula

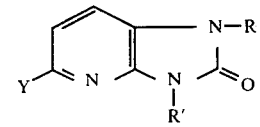

wherein R is alkyl of 1 to 3 carbon atoms and R' is pyridyl and Y is selected from the group consisting of hydrogen and chlorine and their non-toxic, pharmaceutically acceptable acid addition salts.

2. A compound of claim 1 wherein R is methyl.

3. A compound of claim 1 which is selected from the group consisting of 1-methyl-3-(4-pyridyl)-1,3-dihydro-imidazo-(4,5-b)-pyridin-2-one and its non-toxic, pharmaceutically acceptable acid addition salts.

4. A compound of claim 1 which is selected from the group consisting of 1-methyl-3-(3-pyridyl)-5-chloro-1,3-dihydro-imidazo-(4,5-b)-pyridin-2-one and its non-toxic, pharmaceutically acceptable acid addition salts.

5. A compound of claim 1 which is selected from the group consisting of 1-methyl-3-(2-pyridyl)-5-chloro-1,3-dihydro-imidazo-(4,5-b)-pyridin-2-one and its non-toxic, pharmaceutically acceptable acid addition salts.

6. A compound selected from the group consisting of 2-(4-pyridylamino)-3-amino-pyridine, 2-(2-pyridylamino)-3-amino-pyridine and 2(2-pyridylamino)-3-nitro-pyridine and compounds of the formula

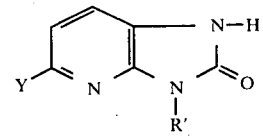

wherein R' is a pyridyl and Y is selected from the group consisting of chlorine and hydrogen and its non-toxic, pharmaceutically acceptable acid addition salts.

7. An antiulcerogenic and antisecretic composition comprising an antiulcerogically and antisecretically effective amount of at least one compound of claim 1 and an inert pharmaceutical carrier.

8. A composition of claim 7 wherein R is methyl.

9. A composition of claim 7 wherein the compound is selected from the group consisting of 1-methyl-3-(4-pyridyl)-1,3-dihydro-imidazo-(4,5-b)-pyridin-2-one and its non-toxic, pharmaceutically acceptable acid addition salts.

10. A composition of claim 7 wherein the compound is selected from the group consisting of 1-methyl-3-(3-pyridyl)-5-chloro-1,3-dihydro-imidazo-(4,5-b)-pyridin-2-one and its non-toxic, pharmaceutically acceptable acid addition salts.

11. A composition of claim 7 wherein the compound is selected from the group consisting of 1methyl-3-(2pyridyl)-5-chloro-1,3-dihydro-imidazo-(4,5-b)-pyridin-2-one and its non-toxic, pharmaceutically acceptable acid addition salts.

12. A method of inducing gastric anti-secretic and antiulcerogenic activity in warm-blooded animals comprising administering to warm-blooded animals a gastric antisecretically and anti-ulcerogenically effective amount of at least one compound of claim 1.

13. A method of claim 12 wherein R is methyl.

14. A method of claim 12 wherein the compound is selected from the group consisting of 1-methyl-3-(4-pyridyl)-1,3-dihydro-imidazo-(4,5-b)-pyridin-2-one and its non-toxic, pharmaceutically acceptable acid addition salts.

15. A method of claim 12 wherein the compound is selected from the group consisting of 1-methyl-3-(3-pyridyl)-5-chloro-1,3-dihydro-imidazo-(4,5-b)-pyridin-2-one and its non-toxic, pharmaceutically acceptable acid addition salts.

16. A method of claim 12 wherein the compound is selected from the group consisting of 1-methyl-3-(2-pyridyl)-5-chloro-1,3-dihydro-imidazo-(4,5-b)-pyridin-2-one and its non-toxic, pharmaceutically acceptable acid addition salts.

17. A method of inducing anorexigenic activity in warm-blooded animals comprising administering to warm-blooded animals an anorexigenically effective amount of compound of claim 1.

18. A method of claim 17 wherein R is methyl.

19. A method of claim 17 wherein the compound is selected from the group consisting of 1-methyl-3-(4-pyridyl)-1,3-dihydro-imidazo-(4,5-b)-pyridin-2-one and its non-toxic, pharmaceutically acceptable acid addition salts.

20. A method of claim 17 wherein the compound is selected from the group consisting of 1-methyl-3-(3-pyridyl)-5-chloro-1,3-dihydro-imidazo-(4,5-b)-pyridin-2-one and its non-toxic, pharmaceutically acceptable acid addition salts.

21. A method of claim 17 wherein the compound is selected from the group consisting of 1-methyl-3-(2-pyridyl)-5-chloro-1,3-dihydro-imidazo-(4,5-b)-pyridin-2-one and its non-toxic, pharmaceutically acceptable acid addition salts.

22. An anorexigenic composition comprising an anorexigenically effective amount of at least one compound of claim 1 and a pharmaceutical carrier.

23. A composition of claim 22 wherein R is methyl.

24. A composition of claim 22 wherein the compound is selected from the group consisting of 1-methyl-3-(4-pyridyl)-1,3-dihydro-imidazo-(4,5-b)-pyridin-2-one and its non-toxic, pharmaceutically acceptable acid addition salts.

25. A composition of claim 22 wherein the compound is selected from the group consisting of 1-methyl-3-(3-pyridyl)-5-chloro-1,3-dihydro-imidazo-(4,5-b)-pyridin-2-one and its non-toxic, pharmaceutically acceptable acid additions salts.

26. A composition of claim 22 wherein the compound is selected from the group consisting of 1-methyl-3-(2-pyridyl)-5-chloro-1,3-dihydro-imidazo-(4,5-b)-pyridin-2-one and its non-toxic, pharmaceutically acceptable acid addition salts.

* * * * *